(12) United States Patent
Thompson et al.

(10) Patent No.: US 6,979,460 B1
(45) Date of Patent: Dec. 27, 2005

(54) VINYL ETHER LIPIDS WITH CLEAVABLE HYDROPHLIC HEADGROUPS

(75) Inventors: David H. Thompson, West Lafayette, IN (US); Jeremy A. Boomer, Lindenhurst, IL (US); Robert Haynes, Annapolis, MD (US)

(73) Assignee: Purdue Research Foundation, West Lafayette, IN (US)

( * ) Notice: Subject to any disclaimer, the term of this patent is extended or adjusted under 35 U.S.C. 154(b) by 495 days.

(21) Appl. No.: 10/031,033

(22) PCT Filed: Jul. 17, 2000

(86) PCT No.: PCT/US00/19430

§ 371 (c)(1),
(2), (4) Date: May 7, 2002

(87) PCT Pub. No.: WO01/05375

PCT Pub. Date: Jan. 25, 2001

Related U.S. Application Data

(60) Provisional application No. 60/146,552, filed on Jul. 30, 1999, provisional application No. 60/144,301, filed on Jul. 16, 1999.

(51) Int. Cl.$^7$ .................. A61K 9/127; C07C 41/00
(52) U.S. Cl. .................. 424/450; 424/1.21; 424/9.321; 424/9.51; 554/79; 554/80; 554/85; 568/579; 568/687; 514/438; 514/461; 514/739
(58) Field of Search .............. 424/450, 1.21, 424/9.321, 9.51, 417; 554/79, 80, 85; 568/579, 568/687; 514/438, 461, 739

(56) References Cited

U.S. PATENT DOCUMENTS 5,277,913 A    1/1994   Thompson et al.

Primary Examiner—Gollamudi S. Kishore
(74) Attorney, Agent, or Firm—Henry D. Coleman; R. Nell Sudol; William J. Sapone

(57) ABSTRACT

A novel amphiphilic lipid compound having a cleavable, vinyl ether linked hydrophilic headgroup is described. Also described are liposomes containing the vinyl ether lipid compound, which may be triggered to release their contents and/or permeablize or fuse with target lipid membranes. The cleavable vinyl ether linkage allows the hydrophilic headgroup to be dissociated from the hydrophobic tailgroup(s) of the lipid compound to facilitate phase transitions in the lipid bilayer.

26 Claims, 7 Drawing Sheets

2-Vinyl-1,3-dioxolane Strategy

| CMPD | R—Li | SOLVENT | E—X | CIS:TRANS | % YIELD |
|---|---|---|---|---|---|
| 1 | nBuLi | pentane | $H_3O^+$ | 35:65 | 71 |
| 2 | nBuLi | 3:2 pentane:ether | $H_3O^+$ | 65:35 | 74 |
| 3 | nBuLi | THF | $H_3O^+$ | 10:90 | 15 |
| 4 | nBuLi | pentane | p-MePhSO$_2$—Cl | 40:60 | 81 |
| 5 | nBuLi | pentane | POCl$_3$ | 35:65 | 46 (phosphate triester) |
| 6 | nBuLi | pentane | (EtO)$_2$(O)P—Cl | 35:65 | 90 |
| 7 | C$_{10}$H$_{21}$—Li | 3:2 pentane:ether | $H_3O^+$ | 70:30 | 57 |
| 8 | C$_{14}$H$_{29}$—Li | 3:2 pentane:ether | $H_3O^+$ | 80:20 | 25 |

VINYL ETHER LIPIDS WITH CLEAVABLE HYDROPHILIC HEADGROUPS

This application claims priority to U.S. Provisional Patent Application No. 60/144,301, filed Jul. 16, 1999 and U.S. Provisional Patent Application No. 60/146,552, filed Jul. 30, 1999.

BACKGROUND OF THE INVENTION

This invention relates to novel amphiphilic compounds with cleavable hydrophilic headgroups and their use in liposomes. More particularly, the invention relates to novel lipid compounds with hydrophilic headgroups linked to the molecule through a vinyl ether linkage, and their use in liposome vesicle formation and the triggered release of the liposomal contents or triggered permeabilization of, or fusion with, target lipid membranes. In another aspect, the invention also relates to triggered cleavage of the headgroups of novel vinyl ether lipid compounds while incorporated in liposomes, to facilitate a phase transition of the liposome to effect the release of liposomal contents and/or the permeabilization of, and/or fusion with, cellular membranes by the liposomes.

Liposomes have been used as drug delivery vehicles with both passive and active-targeting schemes to attempt to site-specifically deliver the contents of the liposome to target tissues in vivo as well as in cell and tissue culture applications. A significant drawback of previous methods of liposomal delivery systems has been constructing liposomes that have sufficient cell culture or in vivo stability to reach desired tissue sites and/or intra-cellular compartments, but will then efficiently release their contents once at the target site.

A wide variety of liposomal release mechanisms activated by light, heat, low pH, or enzymatic activity have been reported and reviewed. See Gerasimov, O. V., Rui, Y., and Thompson, D. H., *Triggered Release from Liposomes Mediated by Physically and Chemically Induced Phase Transitions*, Vesicles, Morton Rosoff, ed., Marcel Dekker, Inc., New York, 1996. One such method described in U.S. Pat. No. 5,277,913 provides for triggered phase changes in liposomes containing plasmalogen or plasmalogen analogs to cause release of the liposomal contents. In that disclosure, the vinyl ether linkage bonding one or both of the hydrophobic tailgroups of the lipids forming the liposome is cleaved by low pH conditions or by oxidation mediated by photoactive sensitizer agents. The cleavage results in one or both of the hydrophobic tailgroups dissociating from the molecule, which causes local changes in the liposome structure leading to leaking of liposomal contents or to fusing of the liposome with adjacent membranes. However, these lipids, with labile vinyl ether linkages joining the hydrophobic tail groups to the remainder of the molecule, have limited sensitivity to desirable triggering conditions, as exhibited by slow liposomal content release rates and/or slow membrane fusion kinetics, to be optimal for many applications. One theory for this is that the labile vinyl ether linkage may distribute in the hydrophobic region of lipid bilayers, where access to protons and oxidative agents is limited.

In that no liposome structure has been found to date that is optimal for all applications, there is a need for new liposome compositions which remain stable in vivo and cell culture until they reach their desired target tissues or cellular compartments, whereupon they may be efficiently triggered to release their contents and/or to permeabilize or fuse with target membranes to deliver the liposomal contents into desired sites. It has been surprisingly found that the vinyl ether lipids of the present invention, having cleavable hydrophilic headgroups, facilitate liposome vesicle formation, and when cleaved under specific conditions at desirable target sites, facilitate liposomal content release and/or permeabilization of or fusion with target membranes.

SUMMARY OF THE INVENTION

It is an object of the present invention to provide novel amphiphilic lipid compounds having acid or oxidatively labile vinyl ether linked hydrophilic headgroups which may be cleaved from the compound by oxidation or acid hydrolysis.

It is an object of another aspect of the present invention to provide lipid vesicles or liposomes containing two or more species, or types, of lipid molecules, at least one of which is a vinyl ether lipid having a cleavable hydrophilic headgroup. In a preferred embodiment of this aspect of the invention, the cleavable hydrophilic headgroups of the vinyl ether lipids cleave from the remainder of the molecule under oxidative and/or acidic conditions and the dissociation of the hydrophilic headgroups causes a local phase transition in the lipid bilayer.

In yet another aspect of the present invention it is an object to provide methods of delivering the contents of a liposome to target tissues, or across a target lipid bilayer membrane by contacting the tissue or lipid bilayer membrane under acidic and/or oxidative conditions, with a liposome comprising at least one type of lipid compound having a cleavable, vinyl ether linked hydrophilic headgroup, under which conditions the hydrophilic headgroups will dissociate from the remainder of the lipid compounds and thereby facilitate the permeabilization of and/or membrane fusion with the target lipid bilayer membrane, thereby releasing the contents of the liposome.

Various of these and other objects are achieved by the vinyl ether lipids with cleavable hydrophilic headgroups according to the present invention and their use in forming liposomes and the use of such liposomes to deliver desired therapeutic or diagnostic agents to desired tissues or cellular sites.

In one aspect of the present invention there are provided novel amphiphilic lipid compounds having a hydrophilic headgroup portion which is linked to the remainder of the molecule through a vinyl ether linkage, and a hydrophobic tailgroup portion, effective to anchor the compound in a lipid film or lipid bilayer membrane.

In a preferred embodiment of the invention, the hydrophilic headgroup is bonded to one double bonded carbon of the vinyl group and the ether oxygen is bonded to the other double bonded carbon in the vinyl group. In another preferred embodiment, one or more hydrophobic tailgroups are bonded either directly to the ether oxygen, or bonded by an ether or ester linkage to a polyalcohol or other linking moiety, which is bonded directly to the ether oxygen. In another preferred embodiment, each of said one or more hydrophobic tailgroups is independently selected from the group consisting of sterol, fatty acid ester, fatty alcohol, sphingosine, ceramide, phosphoglycerolipid, polyisoprenoid, and aryl ether.

In another aspect of the present invention there are provided vinyl ether lipid compounds of the formula

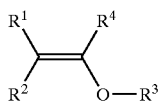

wherein one of either $R^1$ or $R^2$ is a hydrophilic headgroup and the other is hydrogen, a second hydrophilic headgroup, or a crosslinker joining one or more other molecules of the vinyl ether lipid compound, each at the $R^1$ or $R^2$ position; $R^3$ is an organic hydrophobic moiety; and $R^4$ is hydrogen or an electron donating group.

In another aspect of the present invention there are provided liposomes containing two or more species, or types, of lipids, at least one of which is a vinyl ether lipid as described above. The liposome may optionally contain a therapeutic agent or diagnostic agent, which is desired to be transported to and released in a target tissue or across a target lipid bilayer membrane.

In another aspect of the present invention there are provided methods of delivering therapeutic or diagnostic agents to predetermined tissues or across biological membranes by contacting said tissue or cell under oxidative or acidic conditions with a liposome encapsulating the desired agent in a liposome, said liposome comprising at least two different species of lipid compounds, at least one of said lipid compounds being an amphiphilic lipid compound having a acid or oxidatively labile vinyl ether linked hydrophilic headgroup, said acid or oxidative conditions being effective for cleaving said hydrophilic headgroup from the compound.

Related objects and advantages of the present invention will be apparent from the following detailed description of the preferred embodiments.

DESCRIPTION OF THE PREFERRED EMBODIMENTS

Figure 1:
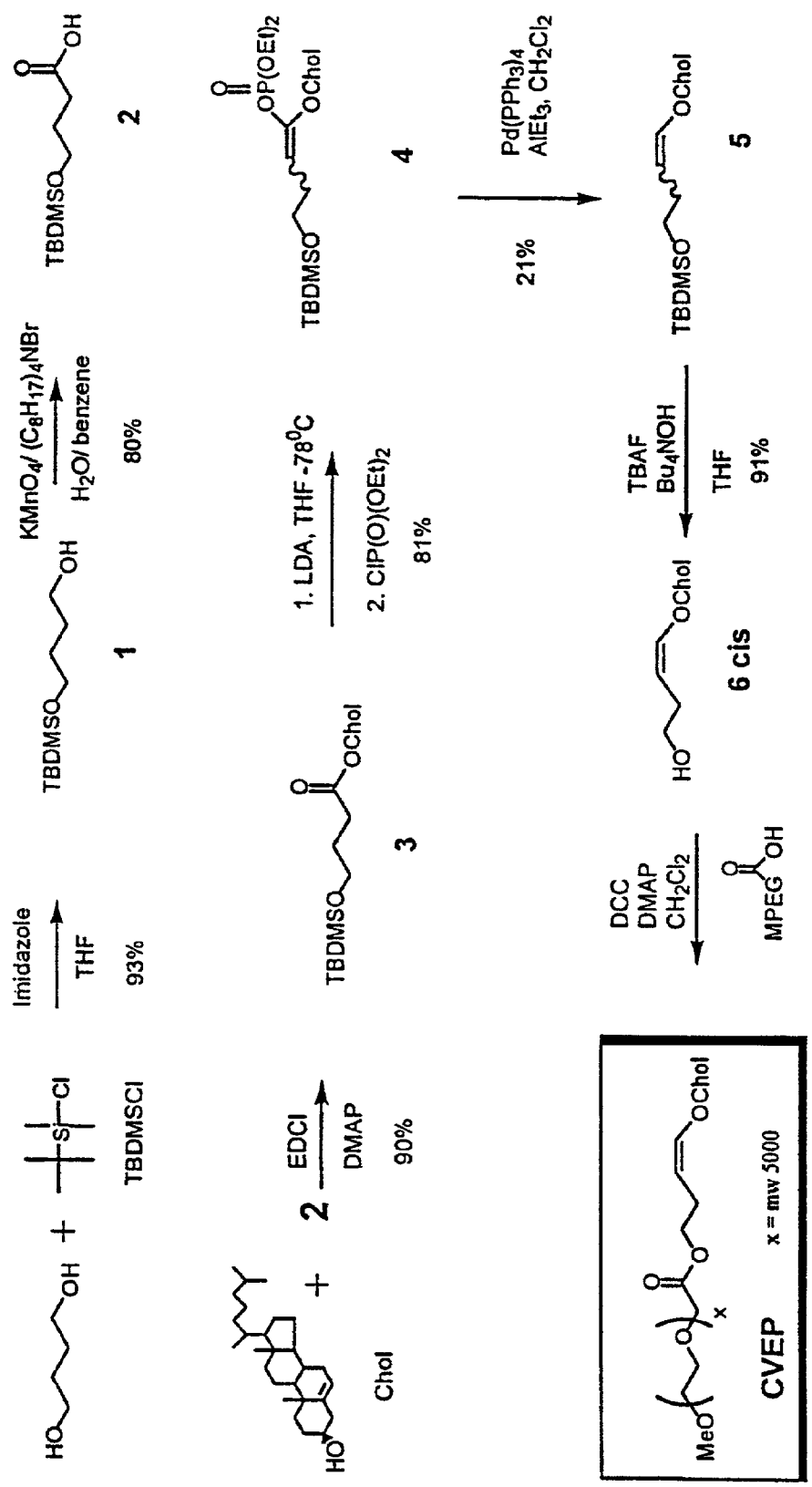
FIG. 1 is a flow chart for the synthesis of CVEP.

For purposes of promoting and understanding the principals of the invention reference will now be made to specific preferred embodiments and specific language will be used to describe the same. These specific descriptions of preferred embodiments are meant by way of illustration only, rather than as limitations on the scope of the present invention. Any alterations and modifications in the described invention, and any further applications of the principals of the invention as illustrated therein are contemplated as would normally occur to one skilled in the art to which the invention relates.

Abbreviations used herein are as follows:
CVEP is 1'-(4'-cholesteryloxy-3'-butenyl)-ω-methoxy-polyethylene[ 112] glycolate,
BVEP is (R)-1,2-di-O-(1'Z,9'Z-octadecadienyl)-glycerl-3-(ω-methoxypolyethylene[ 112] glycolate
DOPE is 1,2-dioleoyl-sn-glycerophosphoethanolamine
DMAP is N,N-dimethyl-4-aminopyridine
EDCI is ethyldimethylaminopropyl carbodiimide
THF is tetrahydrofuran
DMF is dimethylformamide
TBAF is tetrabutylammonium fluoride
TOAB is tetraoctylammonium bromide
TLC is thin layer chromatography As used herein, "amphiphilic" describing a molecule, means having both a water-soluble polar head (hydrophilic) portion and a water-insoluble organic tail (hydrophobic) portion.

As used herein, "lipid" is an inclusive term for fats and fat derived materials, including compounds which are or are related to glycerol esters and ethers, fatty acid esters, fatty alcohols, sterols, and waxes. They may be hydrophobic, or amphiphilic. When amphiphilic, the hydrophilic headgroup may be bonded directly to a hydrophobic tailgroup, such as a sterol, fatty acid or fatty alcohol, or the hydrophilic headgroup may be bonded to one or more hydrophobic tail groups through a linker group, such as, but not limited to a glycerol moiety.

As used herein, "vinyl ether" means a moiety in a compound having two carbon atoms bonded to each other by a carbon—carbon double bond, and at least one ether oxygen bonded to one of said double-bonded carbons atoms.

As used herein, acidic or oxidative conditions for triggering cleavage of the labile vinyl ether bond are to be understood as biologically suitable acidic or oxidative conditions; i.e. conditions compatible with biological systems.

The amphiphilic lipid compounds of the present invention comprise a hydrophobic tail portion effective for anchoring the compound in a lipid mono- or bilayer, a linking segment, which is a vinyl ether moiety bonded through the ether oxygen to the hydrophobic tail portion, and a hydrophilic headgroup bonded to the vinyl ether moiety either cis- or trans- to the vinyl ether oxygen. The hydrophilic headgroup of a vinyl ether lipid compound of the present invention may be cleaved from the remainder of the compound by oxidation or acid hydrolysis of the ether bond.

In one preferred embodiment, the hydrophilic headgroups of the amphiphilic compounds are cis to the ether oxygen. The cis isomers advantageously tend to be 3–10 times more reactive than their corresponding trans-isomers. Mixtures of cis- and trans-isomers may be used and may be blended to advantage to custom tailor the average rate of cleavage of the vinyl ether lipids in a population of liposomes to suit a given application.

Likewise, the hydrophobic and hydrophilic portions of amphiphilic lipids of the present invention may be selected to tailor the lipid to a given application. Hydrophobic tailgroups may be bonded directly to the vinyl ether oxygen of the linking portion of the compound. Alternatively, one or more hydrophobic groups may be bonded to a bridging moiety, which is bonded directly to the vinyl ether oxygen of the linking portion of the compound. By way of example, but without limitation, one or more hydrophobic tailgroups may be bonded through ether or ester linkages to a polyalcohol, as for example glycerol, butane-1,4-diol, or a mono-, di-, or tri-saccharide moiety, which bridging moiety is the then bonded to the vinyl ether oxygen of the linking portion of the compound.

Preferred hydrophobic tailgroups include, but are not limited to, fatty acids and fatty alcohols, particularly $C_5$–$C_{32}$ saturated and mono- or poly-unsaturated fatty acids and alcohols; sterols, particularly cholesterol and its derivatives, as for example, but without limitation, ergosterol, stigmasterol, sitosterol, lanosterol, pregnenolone, cortisol, estradiol, aldosterone, cholecalciferol, and cholic acid; sphingosine; ceramide, phosphoglycerolipids, polyisoprenoids; and aryl ethers, particularly phenolic ethers. Particularly preferred are cholesterol and its derivatives, and glycerol diesters of fatty acids, particularly of $C_{10}$–$C_{24}$ fatty acids, glycerol diethers of fatty alcohols, particularly of $C_{10}$–$C_{24}$ fatty alcohols, and glycerol mixed ether/esters of fatty acids and alcohols, particularly of $C_{10}$–$C_{24}$ fatty acids and alcohols. It is to be understood that the hydrophobic portion of lipids of the present invention may also be other amphiphilic lipids, particularly naturally occuring lipids, as for example, but without limitation, phosphlipids and sphingolipids, provided that the resulting amphiphilic compound is effective in inducing lamellar phase lipid bilayers, and that when the vinyl ether bond is cleaved, the dissociation of the hydrophilic headgroup effects a phase transition which destabilizes the lamellar phase, resulting in liposome leakage or permeablization of or fusion with a target membrane.

Oxidative conditions suitable for cleaving the hydrophilic headgroup include but are not limited to the generation of singlet oxygen by photoexcitation of oxidative sensitizer agents, as for example, but without limitation, bacteriochlorophyll α illuminated with near-infrared radiation at between about 670 nm and about 900 nm. Other suitable oxidative sensitizers include, without limitation, metallophthalocyanines, cyanines, metalloporphyrins, phthalocyanines, porphyrins, phenathiazinequinones, purpurins, chlorins, and other dyes which generate singlet oxygen, such as Rose Bengal, etc, each illuminated by radiation of a wavelength within their respective absorption bands. Sensitizers can be introduced into the target tissues directly, or, in a preferred embodiment, by encapsulating the sensitizer in liposomes formed in part with the vinyl ether lipids of the present invention.

Several in vivo tissues and sub-cellular compartments also have oxidative environments able to cleave the hydrophilic headgroups of the lipid compounds of the present invention, as for example, but without limitation, phagosomes, activated macrophages, lymphocytes, neutrophiles, stratum cornium, epidermis tissue, dermis tissue, and subdermal tissue, and neurons undergoing demyelination.

Acidic conditions suitable for acid hydrolysis of the vinyl ether bond to dissociate the hydrophilic headgroups of the amphiphilic lipid compounds of the present invention include pH less than or equal to 6.5, preferably pH less than or equal to 5.5, and more preferably pH less than or equal to 4.5. Such conditions are typically found in cellular endosomes, ischemic tissues, skin tissues, and tissues in the gastrointestinal tract, among other tissues. Thus, the cleavage of the vinyl ether linked hydrophilic headgroups of lipids of the present invention contained in liposomes may be advantageously triggered by the endocytosis of the liposome followed by the natural acidification of the endosome, leading to the release of the liposomal contents, or depending on the selected liposomal composition, the fusing of the liposomal membrane with the endosomal membrane resulting in the delivery of the liposomal contents into the cytoplasm of the cell.

In another aspect of the present invention there are provided vinyl ether compounds of the formula

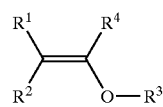

wherein one of either $R^1$ or $R^2$ is a hydrophilic headgroup and the other is hydrogen, a second hydrophilic headgroup, or a crosslinker joining at least one other molecule of the vinyl ether lipid compound at the $R^1$ or $R^2$ position; $R^3$ is an organic hydrophobic moiety; and $R^4$ is hydrogen or an electron donating group.

Preferred vinyl ether lipid compounds of this aspect of the invention include compounds wherein $R^3$ is selected from the group consisting of cholesterol, a cholesterol derivative, sphingosine, a sphingosine derivative, and a group of the formula

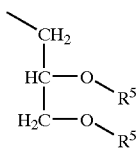

wherein each $R^5$ is independently a hydrophobic group of the formula

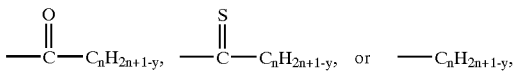

wherein n is an integer from 5 to 32 inclusive; y is an even integer from 2 to 12 inclusive, and wherein y is less than or equal to n.

Other hydrophobic tail groups are known in the art and are suitable for linkage through the ether oxygen of the lipid compounds of the present invention to provide a hydrophobic anchor for the compound in liposomes or other lipid mono- or bilayers.

In alternative embodiments of the present invention, $R^4$ may be either hydrogen or an electron donating group. Electron donating groups enhance the lability of the ether linkage to the hydrophobic tail group portion of the compound. Those skilled in the art may select electron donating groups to tailor the acid and/or oxidative lability of the vinyl ether lipid compound to suit a particular usage. The skilled artisan may tailor the compound to cleave at a higher or lower pH and/or under greater or lesser oxidative conditions, and thereby better control the tissue or cellular location of cleavage and the rate of cleavage of the amphiphilic lipid compounds used in a given liposome population. This advantageously allows for the finer control of the rate of release of liposomal contents and/or the permeabilization of or membrane fusion with target membranes by liposomes containing the present vinyl ether lipid compounds to suit a particular application. Examples of suitable electron donating groups include, but are not limited to, $C_1$–$C_6$ alkoxy, preferably $C_1$–$C_3$ alkoxy, furan, thiophene, and mono-, di- or tri- $C_1$–$C_2$ alkoxy substituted phenyl.

The hydrophilic headgroups of the vinyl ether lipid compounds of the present invention are hydrophilic moieties effective in producing an amphiphilic compound with the selected hydrophobic tail group(s) so as to induce formation of liposomes with other lipids which do not otherwise form stable liposomes under the desired target conditions. The hydrophilic headgroups are likewise effective in stabilizing liposomes in the lamellar phase prior to the cleavage of the headgroups from the compounds. It is to be understood that when $R^1$ and $R^2$ are both hydrophilic headgroups, they are each independently selected from the same set of suitable hydrophilic headgroups.

Exemplary hydrophilic headgroups include, but are not limited to, naturally occurring lipid hydrophilic headgroups, substituted and unsubstituted poly(ethylene glycol), water-soluble polymers with a molecular weight of about 10,000 or less, amino substituted carbamates, mono-, di-, tri-, and oligosaccharides. Preferred hydrophilic headgroups include poly(ethylene glycol), $C_1$–$C_6$ alkoxy poly(ethylene glycol), poly(ethylenimine), N,N-di(aminoethyl)carbamyloxyethyl-, choline, monosaccharide, disaccharide, ethanolamine, phosphatidylcholine, phosphatidylethanolamine, cardiolipin, phosphatidylmonosaccharides, such as phosphatidylinositol, and phosphatidyldisaccharides. Particularly preferred hydrophilic headgroups include poly(ethylene glycol) and $C_1$–$C_6$ alkoxy terminated poly(ethylene glycol) and N,N-di (aminoethyl)carbamyloxyethyl-.

In one preferred embodiment useful in inducing liposome vesicle formation and stabilizing liposomes circulating in cell culture or in vivo prior to triggered cleavage of the hydrophilic headgroup, the hydrophilic headgroup is a poly (ethylene glycol) chain containing an average of between 1 and about 300 glycol units, more preferably an average of between about 10 to about 150 glycol units. In another embodiment, the poly(ethylene glycol) chain contains an average of between about 40 to about 125 glycol units.

When either $R^1$ or $R^2$ is a crosslinker group to another molecule of the vinyl ether lipid compound, two or more lipid compounds according to the present invention may be crosslinked together to obtain a cascading amplification effect. In such an embodiment, the vinyl ether bonds of all the crosslinked molecules would need to be cleaved before the hydrophilic headgroups would dissociate, but then the large number of headgroups dissociating at once induce a larger, potentially more instantaneous, effect on the local membrane structure.

When molecules of vinyl ether lipid compounds of the present invention are crosslinked in this manner, the crosslinker moiety bonds to the individual vinyl ether lipid units at either the $R^1$ or $R^2$ position, with the other position in the respective units being the hydrophilic headgroup moiety. Several vinyl ether lipid units may be crosslinked in this fashion by selecting a crosslinker with a plurality of crosslinking functional moieties, as for example, a polymer with an appropriate funtionality. Suitable crosslinkers include, but are not limited to triethylenediamine, α,ω-polyethylene glycol, α,ω-polyethylenimine, α,ω-polygylcidol, α,ω-polyacrylic acid, polylysine, polyarginine, spermine, and spermidine.

The vinyl ether lipid compounds of the present invention can be synthesized in a variety of methods. One such method begins by protecting one hydroxyl group of 1,4-butanediol with a blocking reagent, such as t-butyldimethylsilylchloride, followed by oxidation of the second hydroxyl to provide a carboxyl group, as for example with potassium permanganate. An ester bond is then formed by a condensation reaction with the carboxy group and a hydroxy group on the desired hydrophobic tailgroup portion, as for example by reaction with cholesterol or the dioleoyl ester of glycerol in DMAP and EDCI. The ester bond is then converted to a vinyl ether bond through a phosphonyl intermediate, followed by reduction with a palladium/aluminum catalyst, as for example, by reacting the ester with n-butyllithium and diisopropylamine, followed by reaction with chlorodiethylphosphate to produce the diethylphosphonyl-1-butene, and then reacting the phosphonyl butene intermediate with tertrakistriphenylphosphate palladium and triethylaluminum in methylene chloride to produce the racemic vinyl ether lipid. Lastly, the blocking group is removed to regenerate a hydroxyl group, which is then condensed with a free carboxy group on the hydrophilic headgroup to yield an amphiphilic lipid compound with a vinyl ether linked hydrophilic headgroup according to the present invention.

Alternatively, a simplified synthetic method to produce the vinyl ether lipid compounds of the present invention, which results in similar or better yields and fewer problematic waste products, is as follows:

2-Vinyl-1,3-dioxolane is reacted with an ω-protected alkyllithium, such as 4'-t-butyldiphenylsilyl-2-(2'-butenyl)-1,2-dioxolane, to effect the vinyl addition of the alkyl group with the opening of the dioxolane ring, forming a vinyl ether group and a reactive oxide ion. Upon completion of the reaction, a weak acid, such as water, or a sulfonyl chloride such as mesyl or tosyl chloride, is added to yield the corresponding alcohol or sulfonate. Substitution of these groups with hydrophobic moieties, via ether, ester, carbamyl, or alkyl groups gives a protected hydrophobic vinyl ether intermediate. This intermediate is then reacted with a fluorous deprotecting agent, as for example, but without limitation, TBAF, hydrofluoric acid, or sodium fluoride. The unprotected intermediate is then reacted with a precursor of the desired hydrophilic headgroup having an active hydroxy, amino, sulfonate, or phosphate group to coupled the headgroup to the vinyl group to yield a vinyl ether lipid with the cleavable linkage in the aqueous region of the membrane interface.

In another aspect of the present invention, there are provided liposomes comprising at least two different species, or types of lipid compounds, at least one of which is an amphiphilic lipid compound having a vinyl ether linked hydrophilic headgroup as described above. Methods for forming lipid vesicles or liposomes, particularly those containing desirable agents such as therapeutic drugs and/or diagnostic indicators, are well known in the art. It is likewise known how to select lipids to provide a general targeting of the liposome for specific tissue or cell types. The present invention provides for the modification for such liposomes or lipid vesicles to facilitate their interaction with biological membranes when the liposomes come in contact with the target tissues or membranes, primarily to allow the delivery of the liposome contents to the target tissue or across the target membrane.

In a preferred embodiment, liposomes are made to include at least one species of vinyl ether lipid compound of the present invention. In a preferred embodiment, the one or more vinyl ether lipid compounds of the present invention constitute between about 0.1% and about 20% of the molar lipid content of the liposomes. More preferably, the liposomes molar lipid content contains between about 1.0% and about 15% vinyl ether lipid compound. In one embodiment of the present invention the liposomes contain between about 3.0% and about 10% vinyl ether lipid on a molar basis of the lipid content. It is to be understood that the vinyl ether lipid concentrations may be the sum of one or more vinyl ether lipid compounds of the present invention as desired for a particular application.

By the controlling the selection of the specific vinyl ether lipid compound or compounds used in the liposome synthesis and their relative concentrations, as well as the selection of other lipids and targeting agents, etc., the skilled artisan can tailor construct liposomes of a given stability for circulation, and of a desired release rate profile or fusogenicity to suit a particular therapeutic or diagnostic indication.

By way of example, but without limitation, it is known that the lipid, DOPE, does not form vesicles, but rather exists in aqueous media in a hexagonal tubular array. When 1–3 mole percent CVEP is added, the lipid mix can form liposomes. About 3–5 mole percent CVEP:DOPE can be used to form liposomes of suitable stability for cell culture uses, whereas about 5–10 mole percent is preferred for in vivo applications. The skilled chemist will be able to select optimum liposome compositions to suit a given application.

Liposomes comprising one or more vinyl ether lipid compounds of the present invention and containing a desired therapeutic or diagnostic agent encapsulated within the liposome may be used to deliver the agent to a desired target tissue or across a biological membrane, as for example delivering the agent to the interior of a living cell within a target tissue. Target tissues or cells are contacted with liposomes encapsulating a desired therapeutic agent or diagnostic agent according to the present invention under acidic or oxidative conditions effective to cleave the vinyl ether bond of the vinyl ether lipids, thereby dissociating the hydrophilic headgroups from the hydrophobic tailgroup portions of the molecules. The dissociation causes a destabilization of the liposome, as for example by a phase transition from the lamellar phase to a hexagonal phase, thereby causing leakage of the liposomal contents into the tissue or cellular site, or a permeabilization of or fusion with a target membrane resulting in releasing the liposomal contents into the cellular compartment across the membrane.

In one embodiment, the liposomes encapsulating a therapeutic or diagnostic agent are designed to be endocytosed by the target cell population. Upon uptake, the endocytic vesicle is naturally acidified, which causes cleavage of the vinyl ether bond of the vinyl ether lipids, dissociating the hydrophilic headgroups therefrom. The dissociation destabilizes the liposome, inducing fusion of the liposomal membrane with the cellular endocytic vesicle membrane resulting in the release of the liposomal contents, including the therapeutic or diagnostic agent, into the cytoplasm of the cell.

In another embodiment, liposomes encapsulating a therapeutic or diagnostic agent are designed to accumulate in a target tissue having an acidic interstitial environment, as for example certain tumor tissues or ischemic tissues. Upon reaching the target tissue, the acidic conditions cause cleavage of the vinyl ether bonds of the vinyl ether lipids, dissociating the hydrophilic headgroups therefrom. The dissociation destabilizes the liposome, inducing the breakdown of the liposome to release the liposomal contents, including the therapeutic or diagnostic agent, into the interstitial fluid of the tissue. Alternatively or in addition, the destabilization may induce fusion of the liposomal membrane with the cellular membrane resulting in the release of the liposomal contents into the cytoplasm of the cells in the target tissue.

In yet another embodiment, the liposomes encapsulating a therapeutic or diagnostic agent also contain an oxidative sensitizer agent, as for example, bacteriochlorophyll α, or an agent that can be activated to induce acidification of the liposome (an acidification agent). The liposomes are designed to accumulate in a predetermined tissue type. When the liposomes reach the target tissue, the oxidative sensitizing agent is excited or the acidifying agent is activated, thereby causing the cleavage of the vinyl ether lipids, dissociating the hydrophilic headgroups therefrom. The dissociation destabilizes the liposome, inducing the breakdown of the liposome to release the liposomal contents, including the therapeutic or diagnostic agent, into the interstitial fluid of the tissue. Alternatively or in addition, the destabilization may induce fusion of the liposomal membrane with the cellular membrane resulting in the release of the liposomal contents into the cytoplasm of the cells in the target tissue.

The following are examples of specific embodiments of the present invention and are illustrative of its principles. They are not to be considered restrictive, but merely representative of the broader invention disclosed.

EXAMPLE 1

Figure 2:
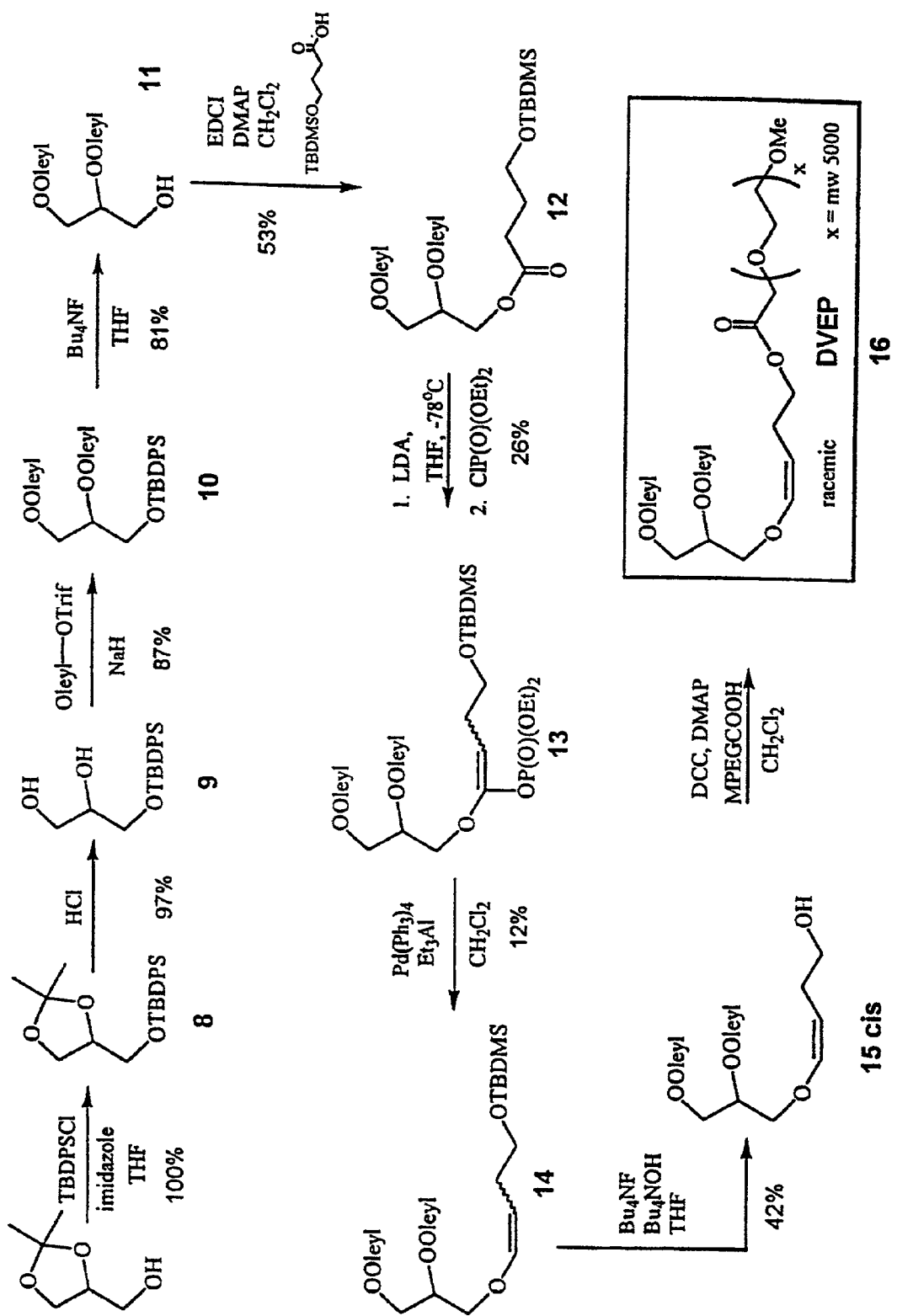
FIG. 2 is a flow chart for the synthesis of DVEP.

Synthesis of CVEP (See FIGS. 1 & 2).

4-o-(t-butyldimethylsilyl)-butane-1-ol (1). A modified procedure using THF instead of DMF as solvent and slow addition of the silyl chloride reagent were used [2]. t-Butyldimethylsilyl chloride (8.57 g, 56.9 mmol) in dry THF (25 ml) was added dripwise to a solution of 1,4-butanediol (20.05 g, 222 mmol; dried in vacuo overnight) and imidazole (4.8 g, 70.5 mmol) in THF (100 ml) at 0° C. over a ~20 min period. The reaction was stirred for 1 hr (turned cloudy after 10 min), warmed to room temperature, and ether (300 ml) added. The solution was then washed with sat. $NH_4Cl$ (2×200 ml) and sat. NaCl (1×200 ml). The ether layer was dried over $MgSO_4$, filtered, evaporated and dried in vacuo yielding 10.8 g of a pale yellow oil. NMR analysis indicated that the product was sufficiently pure to utilize in the subsequent step without further purification. Isolated yield: 93%. TLC: 4:1 hexane:ether, $KMnO_4$ stain; 0.85, 0.35 (product), 0.0; spots at 0.85 & o were faint. $^1$HNMR (ppm, 200 MHz, $CDCl_3$): 0.05 (t, 6H), 0.85 (s, 9H), 1.60 (m, 4H), 2.60 (s, 1H), 3.65 (q, 4H).

4-o-(t-Butyldimethylsilyl) butanoic acid (2) [3]. Potassium permanganate (3.2 g, 20.2 mmol) was dissolved in water (50 ml), stirred vigorously for 10 min, and cooled to 0° C. A benzene solution (40 ml) of 1 (1.98 g, 9.7 mmol) and TOAB (812 mg, 1.5 mmol) was added dropwise via addition funnel over 20 min. The solution was then warmed to room temperature and stirred for 3 h. The remaining potassium permanganate was quenched with sodium bisulfite, producing a two phase mixture with a colorless organic layer. Acetic acid (50 ml, 50%) and benzene (20 ml) were added and the solution extracted. The benzene layer was washed with sat. NaCl (50 ml), then dried over $MgSO_4$, filtered, evaporated, and dried in vacuo. The remaining TOAB was removed via elution through a small silica plug with 2:1 hexane:ether. (Subsequent experiments indicated that tetrabutylammonium bromide works just as well as phase transfer catalyst and is easier to remove in this step). A clear oil (1.65 g, 78% yield) was recovered. TLC: 1:1 hexane:ether, Bromphenol blue stain, 0.65. $^1$H NMR (ppm, 200 MHz, $CDCl_3$): 0.05 (s, 6H), 0.85 (s, 9H), 1.83 (p, J=7 Hz, 2H), 2.44 t, J=9 Hz, 2H), 3.65 (t, J=7 Hz, 2H), 11.57 (bs, 1H). $^{13}$C NMR (ppm, 60 MHz $CDCl_3$): 18.2, 25.8, 27.8, 31, 62.

Cholesteroyl-4-o-(t-butyldimethylsilyl) butanoate (3). Cholesterol (609 mg, 1.58 mmol), 2 (325 mg, 1.49 mmol), and DMAP (20 mg, 0.14 mmol) were dissolved in $CH_2Cl_2$ (15 ml) and the solution cooled to 0° C. EDCI (284 mg, 1.49 mmol) was added, the mixture warmed to room temperature and stirred for up to 10 days (TLC monitoring suggests that 2–3 days is sufficient). The reaction mixture was poured into H$_2$O) (75 ml) and extracted with CH$_2$Cl$_2$ (3×75 ml). The combined CH$_2$Cl$_2$ layers were dried over MgSO$_4$, filtered, evaporated, and dried in vacuo. The crude product was purified via silica gel chromatography (230–400 mesh, 9:1 hexane: ether, 1.5 cm diameter×5 cm height column). A white solid (780 mg) was recovered in 90% yield. TLC: 2:1 hexane:ether, acid char (cholesterol & its derivatives initially stain purple, but turn brown with time), 0.52 (purple/brown, product), 0.13 (purple/brown, cholesterol starting material). $^1$H NMR (ppm, 200 MHz, CDCl$_3$): 0.05 (s, 6H), 0.65 (s 3H), 0.8–2.05 (m, 47H), 2.25–2.4 (m, 4H), 3.65 (t, J=7 Hz, 2H), 4.6 (m, 1H), 5.35 (d, J=5 Hz, 1H). $^{13}$C NMR (ppm, 60 hz, CDCl$_3$): 19–75 multiple peaks, 123, 140.5, 174. MS (Cl, 70 eV): m/z 587 (M+H).

4-o-(t-Butyldimethylsilyl)-1-o-(cholesteryl)-1-o-(1-diethylphosphonyl)-1butene (4) [4]. n-Butyllithium (795 μl, 1.94 mmol, 2.4M in hexane) was added dropwise via syringe to diisopropylamine (453 μl, 3.23 mmol) in THF (250 μl,) at −78° C. and the solution stirred for 30 min. Cholesteroyl-4-o-(t-butyldimethylsilyl) butanoate (758 mg, 1.29 mmol) in THF (3 ml) was then slowly added dropwise via syringe. The solution was stirred for 1 h followed by the addition of chlorodiethylphosphate (373 μl, 2.58 mmol) in HMPA (4.9 ml) in 3 aliquots. The solution turned orange/brown and froze. It was thawed enough to resume stirring, then returned to −78° C. for 10 min. The reaction was then warmed to room temperature and stirred for another 1 h. Ether (50 ml) was added and the reaction mixture filtered through a small silica plug. The solvents were then evaporated and the oil redissolved in ether (75 ml) and washed with 5% NaHCO$_3$ (3×75 ml). The ether layer was dried over MgSO$_4$, filtered, evaporated, and dried in vacuo. The crude product was purified via silica gel flash chromatography (230–400 mesh, 6:1 hexane:ether, 2 cm diameter×16 cm height). Solid product was recovered after evaporation (750 mg, 81% yield). The product was immediately used in the subsequent step without further purification or characterization. TLC: 2:1 hexane:ether, I$_2$ stain, 0.74 (faint, starting material), 0.35 (dark, product), 0.1 (dark, HMPA).

4-o-(t-Butyldimethylsilyl)-1-o-(cholesteryl)-1 butene (5). Tetrakistriphenylphosphine palladium (50 mg, 43.3 μmols) and 4 (960 mg, 1.33 mmol) were added to CH$_2$Cl$_2$ (8 ml) and cooled to 0° C. Triethylaluminum (2.33 ml, 2.33 mmol; 1.0 M in hexane) was then added dropwise via syringe. The solution was stirred at 0° C. for 1 h before warming to room temperature and stirring for an additional 3 h. The crude mixture was purified via silica gel flash chromatography (230–400 mesh, 8:1 hexane:ether, 2 cm diameter×12 cm height) yielding a mixture of product and cholesteroyl-4-o-(t-butyldimethylsilyl) butanoate. This mixture was again separated via silica gel flash chromatography (230–400 mesh, 14:1 hexane:ether, 2 cm diameter×25 cm height). A white solid was recovered (160 mg, 21% yield) as a 75:25 cis:trans mixture. TLC: 8:1 hexane:ether, acid char, 0.8 (dark, product), 0.75 (dark, ester), 0.15 (dark, vinyl phosphate starting material). $^1$H NMR (ppm, 200 MHz, CDCl$_3$): 0.5 (s, 6H), 0.65 (s, 3H), 0.8–2.05 (m, 47H), 2.25–2.4 (m, 3H), 3.45 (m, 1H), 3.6 (t, J=12 Hz, 2H), 4.4 (dt, J$_1$=6 Hz, J$_2$=9 Hz, 0.75H), 4.85 (dt, J$_1$=14 Hz, J$_2$=9 Hz, 0.25H), 5.35 (m, 1H), 6.05 (dt, J$_1$=6 Hz, J$_2$=3 Hz, 0.75H), 6.15 (dt, J$_1$=14 Hz, J$_2$=2 Hz, 0.3H).

4-o-(Cholesteryl)-3Z-buten-1-ol (6). TBAF (210 μl, 210 mmol, 1.0 M in THF) and 1.0 ml TBAOH were added via syringe to 5 (40 mg, 70 μmol) in THF (3 ml). The reaction was run for 12 h then filtered through a small silica plug with ether, the solvent evaporated, and the mixture purified by silica gel flash chromatography (230–400) mesh, 8:1 hexane:ether, 1.5 cm diameter×15 cm height) to give 4-cholestoxy-3Z-buten-1-ol (29 mg, 91% yield) and 4-cholestoxy-3E-buten-1-ol (1.5 mg, 4% yield). TLC: 2:1 hexane:ether, acid char, 0.63 (faint, starting material), 0.18 (dark, cis product), 0.14 (dark, trans product). 6cis: $^1$H NMR (ppm, 200 MHz, C$_6$D$_6$): 0.65 (s, 3H), 0.8–2.05 (m, 47H), 2.3–2.5 (m, 3H), 3.35 (m, 1H), 3.6 (t, J=12 Hz, 2H), 4.4 (dt, J$_1$=6 Hz, J$_2$=9 Hz, 1H), 5.35 (m, 1H), 6.05 (dt, J$_1$=6 Hz, J$_2$=3 Hz, 1H). 6trans: $^1$H NMR (ppm, 200 MHz, C$_6$D$_6$): 0.65 (s, 3H), 0.8–2.05 (m, 50H), 2.4–2.5 (m, 2H), 3.35 (t, J=12 Hz, 2H), 3.5 (m, 1H0, 4.95 (dt, J$_1$=14 Hz, J$_2$=9 Hz, 1H), 5.35 (m, 1H), 6.15 (dt, J$_1$=14 Hz, J$_2$=2 Hz, 1H). MS (CI): m/z 457 (M+H).

4-o-Cholesteryl-(3Z-buten-1-yl)-polyethylene [125] glycolate (CVEP, 7). 4-Cholestoxy-3Z-buten-1-ol (28 mg, 61.3 μmol), M-PEG-acid (MW 5000, 278 mg, 55.7 μmol, Shearwater Polymers), DCC (13.77 mg, 66.9 μmol), and DMAP (10 mg, 18.8 μmol) were added to CH$_2$Cl$_2$ (2 ml) and stirred for 4 d. The dicyclohexylurea sideproduct crystals were then removed by filtration and the solvent concentrated to 2 ml. The concentrate was then dripped into cold ether and the ether solutions centrifuged at 3500 g for 10 min. The ether was then decanted and the pellet washed with fresh ether. This process was repeated 5 more times before the pellet was dissolved in CH$_2$Cl$_2$, evaporated to a dry film, dissolved in 2 ml 18 MΩ Millipore H$_2$O and lyophilized to give 215 mg (71% yield) of PEG containing product. $^1$H NMR indicates the presence of vinyl ether (6.1 ppm), PEG (3.5 ppm), and cholesterol (0.7–2.5 ppm) resonances in approximately the correct ratios.

rac-2,2-Dimethyl-1,3-dioxolane-4-t-butyldiphenylsilyl methanol (8) [5]. (S)-(+)-2,2 Dimethyl-1,3-dioxolane-4-methanol (26.5 g, 200.5 mmol) and imidazole (21.1 g, 309.9 mmol) were dissolved in THF (250 ml). t-Butyldimethylsilyl chloride (61.0 g, 222.6 mmol) was added dropwise via addition funnel over 15 min. A white precipitate formed with the production of a mild exotherm. The reaction was stirred for 2 h then divided into two 175 ml portions. Each portion was added to ether (700 ml) and extracted with H$_2$O (3×600 ml). The combined ether layers were dried over MgSO$_4$, filtered, evaporated, and dried in vacuo to give a faint yellow oil (77.1 g, 100% yield). Although this material contained traces of silanol sideproduct and imidazole, it was judged to be sufficiently pure for direct use in the subsequent reaction. TLC: 1:1 hexane:ether, UV, 0.6 (dark, product), 0.53 (faint, SiOH). $^1$H NMR (ppm, 200 MHz, CDCl$_3$), 1.1 (s, 9H), 1.38 (s, 3H), 1.42 (s, 3H), 3.75 (m, 2H), 3.86 (m, 1H), 4.1 (m, 1H), 4.22 (m, 1H), 7.43 (m, 6H), 7.70 (m 4H).

rac-3-t-Butyldiphenylsilylpropanetriol (9) [6]. 8 (13.0 g, 35.1 mmol) was dissolved in ethanol (100 ml), followed by the addition of concentrated HCl (7 ml) and H$_2$O (10 ml). The reaction was run for 12 min before quenching with 4 M NaOH (100 ml) and product extraction with ether (3×100 ml). The ether layer was then dried over MgSO$_4$, filtered, evaporated, and dried in vacuo. The crude reaction mixture was then purified via silica gel chromatography (60–200 mesh, 2 cm diameter×5 cm height) using 1:1 hexane:ether to elute the starting material (4.8 g), followed by a step gradient of ethyl acetate to elute the product (7.1 g, 61% yield; 97% yield based on converted starting material). TLC: 1:1 hexane:ether, UV KMnO$_4$, 0.65 (faint, UV only, starting material), 0.16 (dark, UV and KMnO$_4$, product). $^1$H NMR (ppm, 200 MHz, CDCl$_3$): 1.1 (s, 9H), 2.05 (bs, 2H), 3.6–3.9 (m, 5H), 7.43 (m, 6H), 7.70 (m 4H).

rac-1,2-Dioleyl-3-t-butyldiphenylsilylglycerol (10) [7.8]. Sodium hydride (1.0041 g, 25 mmol, 60% dispersion in mineral oil) was washed with THF (3×10 ml) prior to the addition of THF (20 ml) and 9 (1.9442 g, 5.9 mmol). After gas evolution ceased (~10 min) oleyl triflate was added (5.03 g, 12.6 mmol) and the reaction stirred until complete within 1 h. The solution was evaporated to dryness, redissolved in hexane, and filtered through a small silica plug with hexane. The hexane eluent was evaporated and dried in vacuo to give a clear viscous oil (4.26 g, 87% yield). TLC: 2:1 hexane:ethyl acetate, UV & acid char, 0.75 (dark, UV product). $^1$H NMR (ppm, 200 MHz, CDCl$_3$): 0.90(t, J=6 Hz, 6H), 1.05 (s, 9H), 1.3 (bs, 44H), 1.55 (m, 4H), 2.0 (m, 8H), 3.3–3.75 (m, 9H), 5.35 (t, J=10 Hz, 4H), 7.43 (m, 6H), 7.70 (m 4H).

rac-1,2-Dioleylglycerol (11). TBAF (7.3 ml, 7.2 mmol, 1.0M in THF) was added to a solution of 10 (2.043 g, 25 mmol) in THF (35 ml). TBAOH (0.1 ml) was then added and the reaction run for 10 h. The solution was then evaporated and the crude product mixture purified via silica gel chromatography (60–200 mesh, 10:1 hexane:ether, 3 cm diameter×20 cm height) to give 1.2 g of a viscous oil (81% yield). TLC: 6:1 hexane:ether, UV & acid char, 0.3 (dark, UV only, SiOH), 0.22 (dark, acid char only, product). $^1$H NMR (ppm, 200 MHz, CDCl$_3$): 0.90 (t, J=6 Hz, 6H), 1.3 (bs, 44H), 1.58 (m, 4H), 2.0 (m, 8H), 2.2 (t, J=5 Hz, 1H), 3.4–3.8 (m, 9H), 5.35 (t, J=5 Hz, 4H).

rac-1,2-Dioleyl-3-(4'-t-butyldiphenylsiloxybutanoate) glycerol (12). 1,2-Dioleyl-rac-glycerol (2.23 g, 3.76 mmol), 2 (0.781 g, 3.58 mmol), and DMAP (20 mg, 0.14 mmol) were dissolved in CH$_2$Cl$_2$(15 ml). EDCI (1.03 g, 5.37 mmol) was then added and the reaction stirred for 2 d. The product mixture was poured into H$_2$O (50 ml) and extracted with CH$_2$Cl$_2$ (3×50 ml). The combined organic layers were dried over MgSO$_4$, filtered, evaporated, and dried in vacuo. The crude product was purified via silica gel flash chromatography (230–400 mesh, 8:1 hexane:ether, 2 cm diameter×25 cm height) to give 1.05 g product (53% yield based on consumed starting material) and 751 mg starting material. TLC: 2:1 hexane:ether, I$_2$ stain, 0.71 (dark, product), 0.51 (impurity), 0.41 (dark, starting material). $^1$H NMR (ppm, 200 MHz, CDCl$_3$): 0.05 (s, 6H), 0.90 (m, 15H), 1.3 (bs, 44H), 1.55(m, 4H), 1.82 (p, J=10 Hz, 2H), 2.0 (m, 8H), 2.4 (t, J=10 Hz, 2H), 3.35–3.65 (m, 9H), 4.0–4.13 (dd, J=8 Hz, H=6 Hz, 1H), 4.17–4.27 (dd, J=9 Hz, J=6 Hz, 1H), 5.32 (t, J=5 Hz, 4H). MS (CI): m/z 793 (M+H).

Vinyl phosphate of rac-1,2-dioleyl-3-(4'-t-butyldiphenylsiloxybutanoate)glycerol (13). nBuLi (635 µl, 1.55 mmol) was added dropwise via syringe to a solution of diisopropyl amine (362 µl, 2.58 mmol) in THF (200 µl) at −780° C. The mixture was stirred for 30 min then a THF solution of 12 (820 mg, 1.03 mmol) was added dropwise via syringe and stirred for 1 h. Diethylchlorophosphate (298 µl, 2.06 mmol) in HMPA (10.5 ml) was then added in 3 aliquots, after which the reaction mixture turned orange and froze. The mixture was then warmed to room temperature and stirred 1 h before filtering through a small silica plug with anhydrous ether. The filtrate was evaporated, redissolved in ether (200 ml), and extracted with 5% NaHCO$_3$ (2×200 ml). The ether layer was then dried over MgSO$_4$, filtered, evaporated, and dried in vacuo. The crude mixture was purified via silica gel chromatography (230–400 mesh, 3.5 cm diameter×12 cm height, 8:1 hexane:ether to elute starting material, 4:1 hexane:ether to elute the product) to give 250 mg of product (27% yield). TLC: 2:1 hexane:ether, I$_2$ stain, 0.75 (dark, product), 0.33 (impurity), 0.23 (dark, product).

rac-1,2 Dioleyl-3-(4'-t-butyldiphenylsiloxy-1'butenyl)-glycerol (14). Tetrakistriphenyl-phosphine palladium (40 mg, 34.6 µmol) and 13 (250 mg, 269 µmol) were dissolved in 3 ml CH$_2$Cl$_2$ and cooled to 0° C. Triethylaluminum (471 µl, 471 µmol, 1M hexane solution) was added dropwise via syringe. The reaction was warmed to room temperature and stirred for 4 h. The product mixture was filtered through a small silica plug with anhydrous ether, the filtrate evaporated, and dried in vacuo. The crude mixture was purified via silica gel chromatography (60–200 mesh, 8:1 hexane:ether, 2 cm diameter×10 cm height). Fractions containing the product and ester (fastest eluting material) were combined, evaporated, and rechromatographed (230–400 mesh silica gel, 14:1 hexane:ether, 2 cm diameter×27 cm height). The product (25 mg, 12% yield) and 12 (100 mg) were recovered. TLC: 14:1 hexane:ether, I$_2$ stain, 0.75 (dark, 14), 0.50 (medium, 12). $^1$H NMR (ppm, 200 MHz, CDCl$_3$): 0.05 (s, 6H), 0.85 (m, 15H), 1.30 (m, 44H), 1.58 (m, 4H), 1.82 (p, J=7 Hz, 2H), 2.0 (m, 8H), 2.2–2.4 (m 2H), 3.35–3.85 (m, 9H), 4.05 (t, J=8 Hz, 1H), 4.35 (dt, J$_1$=6 Hz, J$_2$=9 HZ, 0.65H), 4.72 (dt, J$_1$=12 Hz, J$_2$=9 Hz, 0.35H), 5.35 (t, J=5 Hz, 4H), 5.98 (dt, J$_1$=6 Hz, J$_2$=3 Hz, 0.65H), 6.28 (dt, J$_1$=14 Hz, J$_2$=2 Hz, 0.35H).

rac-1,2-Dioleyl-3-(4'-hydroxy-1'-butenyl)-glycerol (15). TBAF (50 µl, 80 µmol, 1.0M in THF), and TBAOH (0.5 ml) were added to 14 (25 mg, 32.2 µmol) in THF (4 ml) and stirred for 24 h. The mixture was then filtered through a small silica gel plug with ether, the filtrate evaporated, and the residue dried in vacuo. The crude mixture was separated via a silica gel chromatography (Pasteur pipette minicolumn 0.5 cm diameter×4 cm height, 8:1 hexane:ether) to give pure 15cis (9 mg) and 2 mg of a 86:14 15 trans:15cis mixture as colorless oils. Overall yield: 52%. TLC 14:1 hexane:ether, I$_2$ stain, 0.68 (faint, 14) 0.33 (impurity), 0.28 (dark, 15cis), 0.24 (medium, 15trans). 15cis $^1$H NMR (ppm, 200 MHz, C$_6$D$_6$): 0.85 (m, 6H), 1.30 (m, 44H), 1.58 (m, 4H), 2.1 (m, 8H), 2.4 (m 2H), 3.25–3.4 (m, 2H), 3.4–3.63 (m, 7H), 3.7–3.83 (m, 2H), 4.35 (dt, J$_1$=6 Hz, J$_2$=9 Hz, 1H), 5.35(t, J=5 Hz, 4H), 6.0 (dt, J$_1$=6 Hz, J$_2$=3 Hz, 1H). 15trans $^1$H NMR (ppm, 200 MHz, C$_6$D$_6$): 0.85 (m, 6H), 1.30 (m, 44H), 1.58 (m, 4H), 1.8 (m 2H), 2.1 (m, 8H), 3.25–3.4 (m, 2H), 3.4–3.63 (m, 7H), 3.7–3.83 (m, 2H), 4.72 (dt, J$_1$=12 Hz, J$_2$=9 Hz, 1H), 5.35 (t, J=5 Hz, 4H), 6.30 (dt, J$_1$=14 Hz, J$_2$=2 Hz, 1H).

rac-1,2-Dioleyl-3-(4'-hydroxy-1'-butenyl)-glyceryl polyethylene [125] glycolate (DVEP, 16). M-PEG-acid (MW 5000, 62 mg, 12.4 µmol, Shearwater Polymers), 15cis (9 mg, 13.6 µmol), DCC (3 mg, 14.6 µmol), and DMAP (1 mg, 8.2 mmol) were added to CH$_2$Cl$_2$ (2 ml) and stirred for 3 d. At the end of the reaction, the crystalline dicyclohexylurea side product was removed by filtration and the solvent concentrated to 2 ml. The concentrate was then dripped into cold ether and the ether solution centrifuged at 3500 g for 10 min. The ether was then decanted and the pellet washed with fresh ether; this process was repeated five more times. The pellet was then dissolved in CH$_2$Cl$_2$ and evaporated to a dry film.

CVE-DC, 17. 2,2'-Dipyridyl carbonate, 6, and triethylamine were stirred for 3 d in 10 ml CH$_2$Cl$_2$. The reaction mixture was extracted with 25 ml NaHCO$_3$, followed by 25 ml saturated NaCl. The CH$_2$Cl$_2$ layer was dried over Na$_2$SO$_4$, filtered, and evaporated. The resulting oil was dissolved in CH$_2$Cl$_2$ (10 ml). 1,5-Diphalamidyldiethylenetriamine (315 mg, 0.868 mmol) was added and the reaction stirred for 3 d. The solution was evaporated and the crude mixture purified via flash chromatography (3:2 hexane:ether), yielding 350 mg of a clear oil (69% yield). This product was dissolved in 60 ml methanol, hydrazine hydrate added, and the reaction mixture stirred for 2 d. The solution was then evaporated, yielding an off white precipitate. Chloroform (50 ml) was added and the precipitate side product removed via filtration. The filtrate was evaporated and dried in vacuo overnight yielding a faint yellow oil.

DVE-DC, 18. This derivative was prepared in the same manner as for 17, except that 15 was used in the 2,2'-dipyridyl carbonate coupling reaction.

EXAMPLE 2

Methoxy-, Furanyl-, Thiophen-, and 4-Methoxyphenyl-Derivatives of CVEP

Derivatives of CVEP having methoxy, furanyl, thiophen, or 4-methoxyphenyl substitution on the vinyl moiety, gem to the ether oxygen are prepared via the 2-X-2-vinyl-1,3-dioxolane route, where X=methoxy, furanyl, thiophen, or 4-methoxyphenyl. The synthesis of these materials begins with the formation of the corresponding 1-X-propenone in good yields using a Mannich coupling and Hoffman elimination scheme. (See V. J. Gutzmann, P. Messinger, *Arch. Pharm.* 1995, vol. 328, pg. 523–525, or P. Messinger, *Arch. Pharm.* 1973, vol. 306, pg. 603–610.) Tin-catalyzed acetalization with ethylene glycol gives the 2-X-2-vinyl-1,3-dioxolane precursor which is subsequently reacted under Barbier conditions (adding a mixture of the alkyl chloride and dioxolane compounds dropwise to the lithium compound in THF at 0—-20° C. with stirring) with 2-oxo-2-chloro-1,3,2-dioxaphospholane. These species are then coupled to a selected hydrophobic segment using a chloroalkane derivative (RCl), and the dioxaphospholane rings are then opened with trimethylamine to generate an electron-rich vinyl ether product bearing a phosphonocholine headgroup (i.e. $Me_3N^+$—$CH_2CH_2$—$OPO^-(O)$ $CH_2CH$=$CXOR$).

EXAMPLE 3

Alternative Synthesis of CVEP

4'-t-Butyldiphenylsilyl-2-(2'-butenyl)-1,3-dioxolane was reduced with lithium. Aqueous workup then produced 1-(2'-hydroxyethoxy)-4-t-butyldiphenylsilyl-1-buten-4-ol in ~60% yield. Alkylation of this intermediate using sodium hydride/cholesteryl chloride, followed by fluorous ion mediated silyl deprotection and EDCI-mediated coupling ω-methoxypoly(ethyleneglycol), gave the hydroxyethyl derivative of CVEP in moderate yield.

EXAMPLE 4

Liposome Vesicle Preparation

DOPE and the labile PEG lipid were co-dissolved in chloroform that had been prefiltered through a 2.53 cm plug of anhydrous sodium carbonate to remove traces of acid and water from the solvent. This solution was evaporated under a gentle stream of $N_2$ and further dried under vacuum (<200 μ, 4 h). Vesicles were formed by hydrating the lipid film in the presence of 50 mM calcein using five $LN_2$ freeze-thaw-vortex cycles. This suspension was then extruded at 50° C. through two 100 nm track-etch polycarbonate membrane filters [9]. Extraliposomal calcein was removed using a single pass through a 40 cm Sephadex G-50 gel column equilibrated with 150 mM NaCl. The fraction eluting at the void volume was collected and stored at 8° C. until use. Light-sensitive vesicles were prepared in the same manner, except that bacteriochlorophyll a (Bchl) was codissolved in the chloroform lipid solution. Other agents or mixtures of agents, such as therapeutic compounds or diagnostic agents, are substituted for calcein in the above protocol resulting in liposomal encapsulation of the substituted agent.

EXAMPLE 5

Triggered Release Assay

Vesicle release of the liposomes made in example 4 above, was monitored at 37° C. as a function of time using the calcein fluorescence dequenching assay [10]. Acid-trigged release was initiated by dilution of the vesicles into an acidic buffer solution as described by Gerasimov et al [10]. Light-triggered release was promoted by aerobic illumination (800 nm, 1 W) of a continuously stirred 1 cm quartz cuvette with a SDL 820 diode laser coupled to an optical fiber [11]. The fiber was mounted perpendicular to the cuvette surface to produce a spot of ~3 mm diameter. Both triggering methods were conducted either in the absence or presence of ten-fold excess of egg phosphatidylcholine (EPC) vesicles as a membrane "sink".

Results

Figure 3:
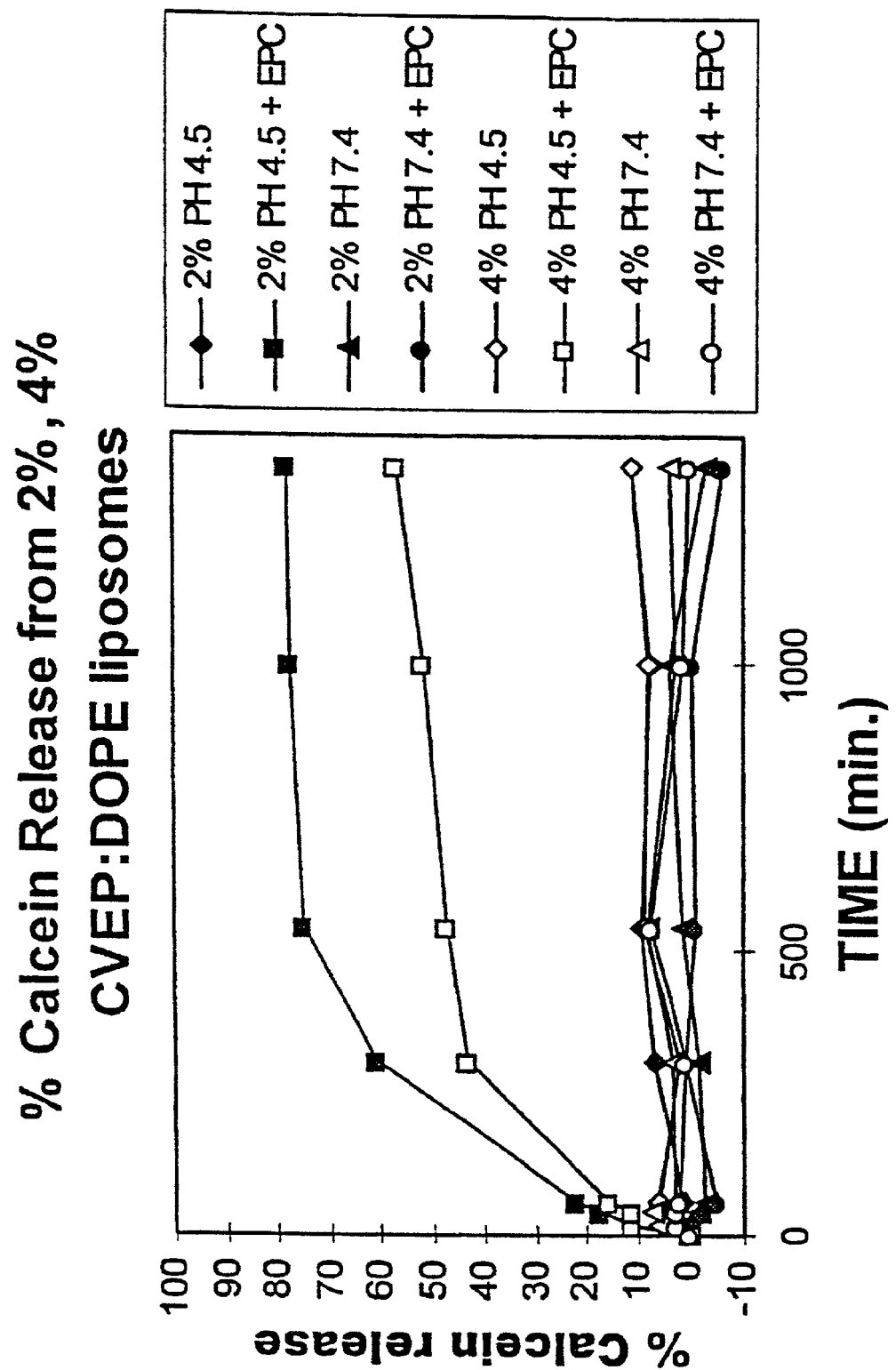
FIG. 3 is a comparison of calcein release from CVEP: DOPE liposomes under acidic conditions.
Figure 4:
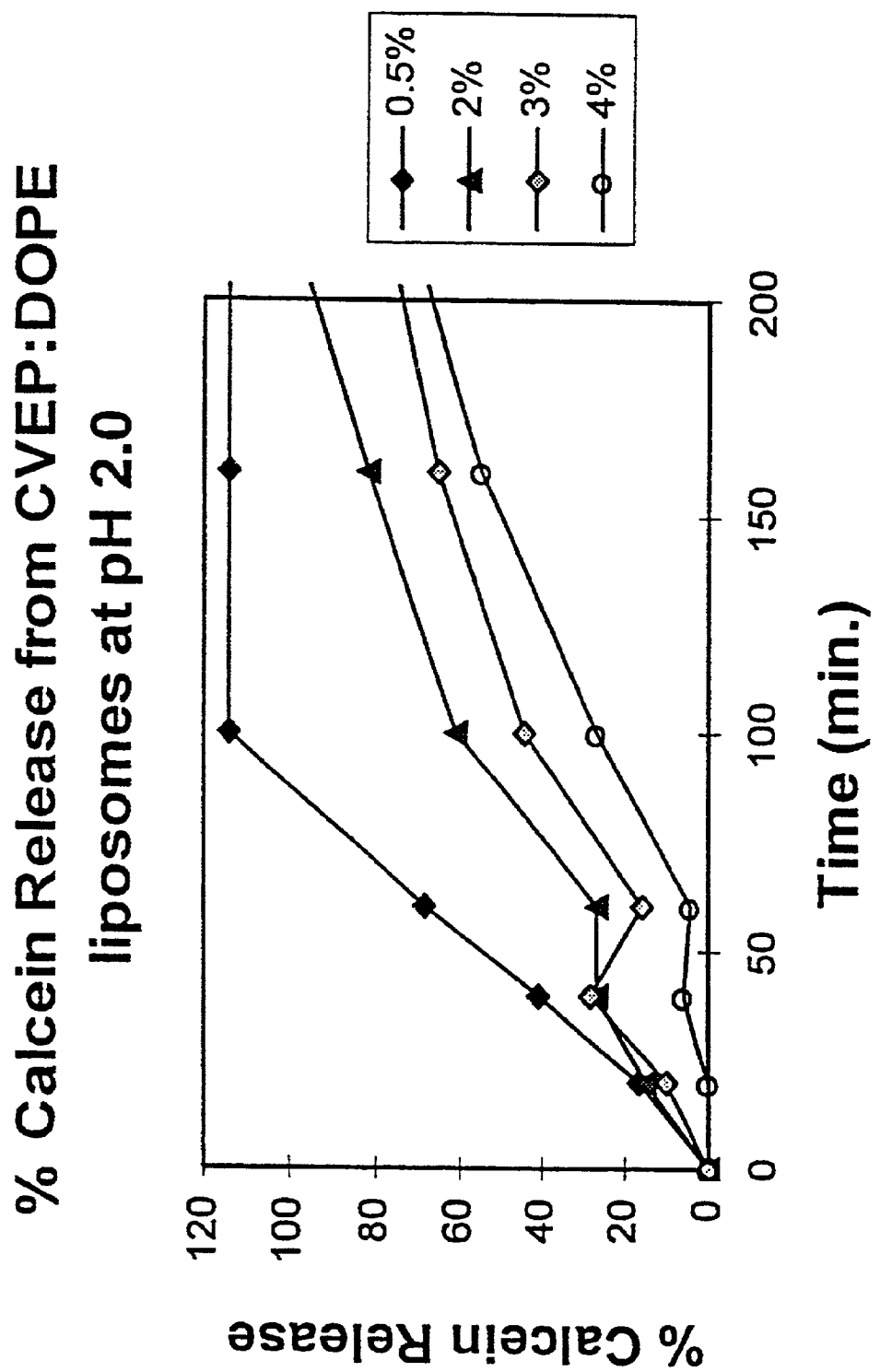
FIG. 4 is a comparison of the release of calcein from DOPE liposomes containing varying concentrations of CVEP.

Acid-triggered Release. The calcein release properties of 98:2 and 96:4 DOPE:CVEP vesicles at pH 7.4 and 4.5, both in the presence and absence of sink EPC vesicles, are shown in FIG. 3. These data suggest the following trends: (i) very little contents leakage is observed at neutral pH, regardless of whether sink EPC is present or not, (ii) calcein leakage occurs in the presence of sink EPC at pH 4.5, (iii) very little contents leakage is observed at pH 4.5 in the absence of sink EPC, and (iv) the rate of calcein leakage under sink conditions at pH 4.5 is dependent upon the vesicle CVEP content, with lower loadings producing more rapid release rates. The last observation is further illustrated in FIG. 4, where DOPE:CVEP vesicles with varying CVEP content were prepared and analyzed for calcein release rate pH 2.0. A strong dependence on release rates was observed, with the half life for release (i.e. $t_{50\% \ release}$) measured as 45, 90, 120, and 155 min for 0.5, 2, 3, and 4% CVEP loadings, respectively. This data clearly indicates that the release rate profiles can be "tuned" by controlling the DOPE:CVEP ratio in the vesicle formulation.

Figure 5:
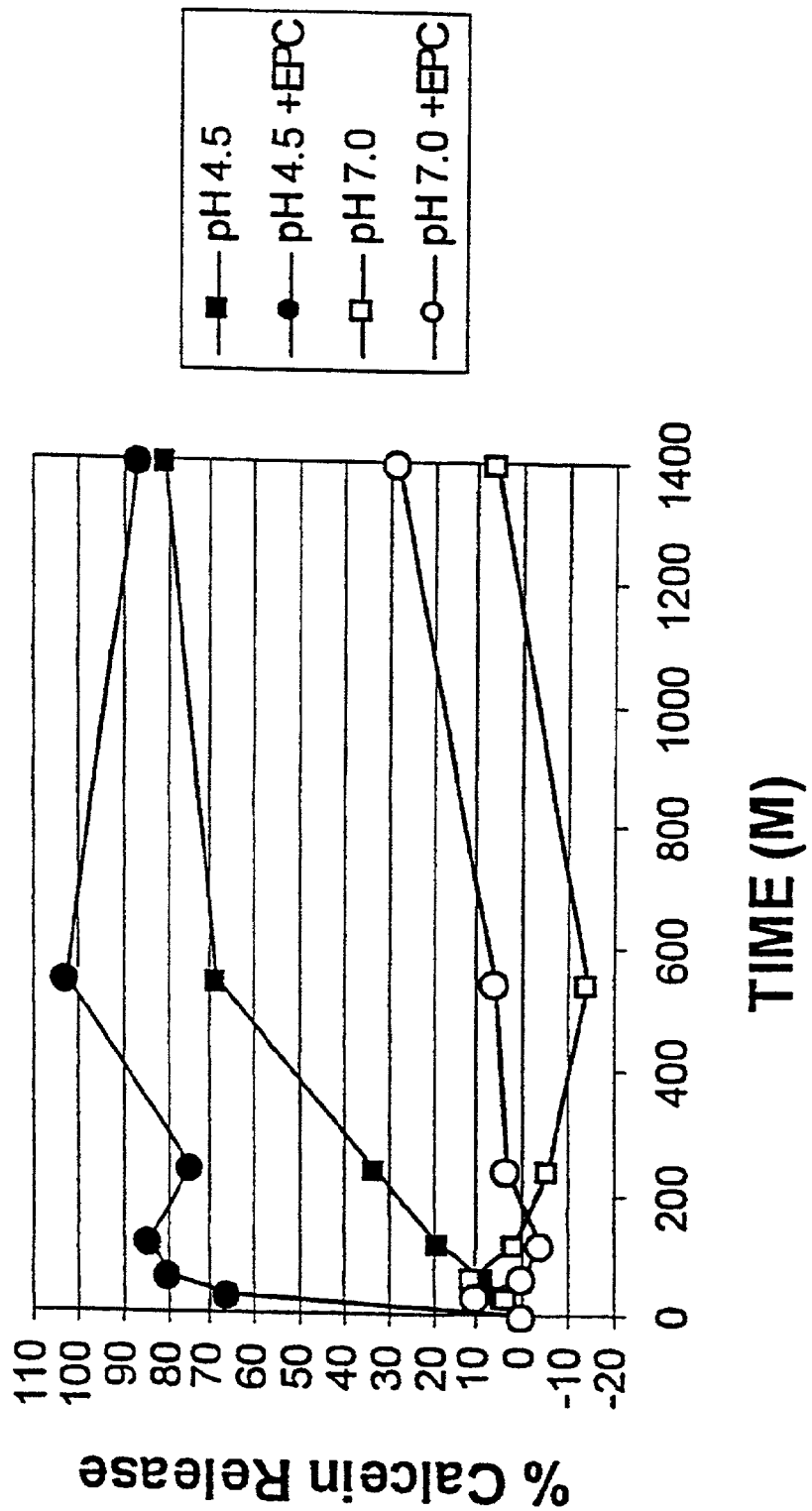
FIG. 5 is a comparison of calcein release from CVEP: DOPE liposomes under acidic conditions in the presence of sink liposomes.

The release rate properties of 98:2 DOPE:DVEP vesicles FIG. 5) demonstrates that DVEP shares some of the characteristics of DOPE:DVEP vesicles, namely the lack of leakage at pH 7.4, regardless of whether sink EPC is present or not. Two properties of this compound differ from the CVEP case: (I) the DVEP release rates are much faster at pH 4.5 than for CVEP at identical loadings (i.e. $t_{50\% \ release}$=23 and 220 min for DVEP and CVEP, respectively) and (ii) significant release occurs in the absence of sink EPC at pH 4.5 in this system ($t_{50\% \ release}$≈3 h). These results suggest that this compound will be most useful in applications requiring rapid triggering, even in the absence of sink membrane material.

Figure 6:
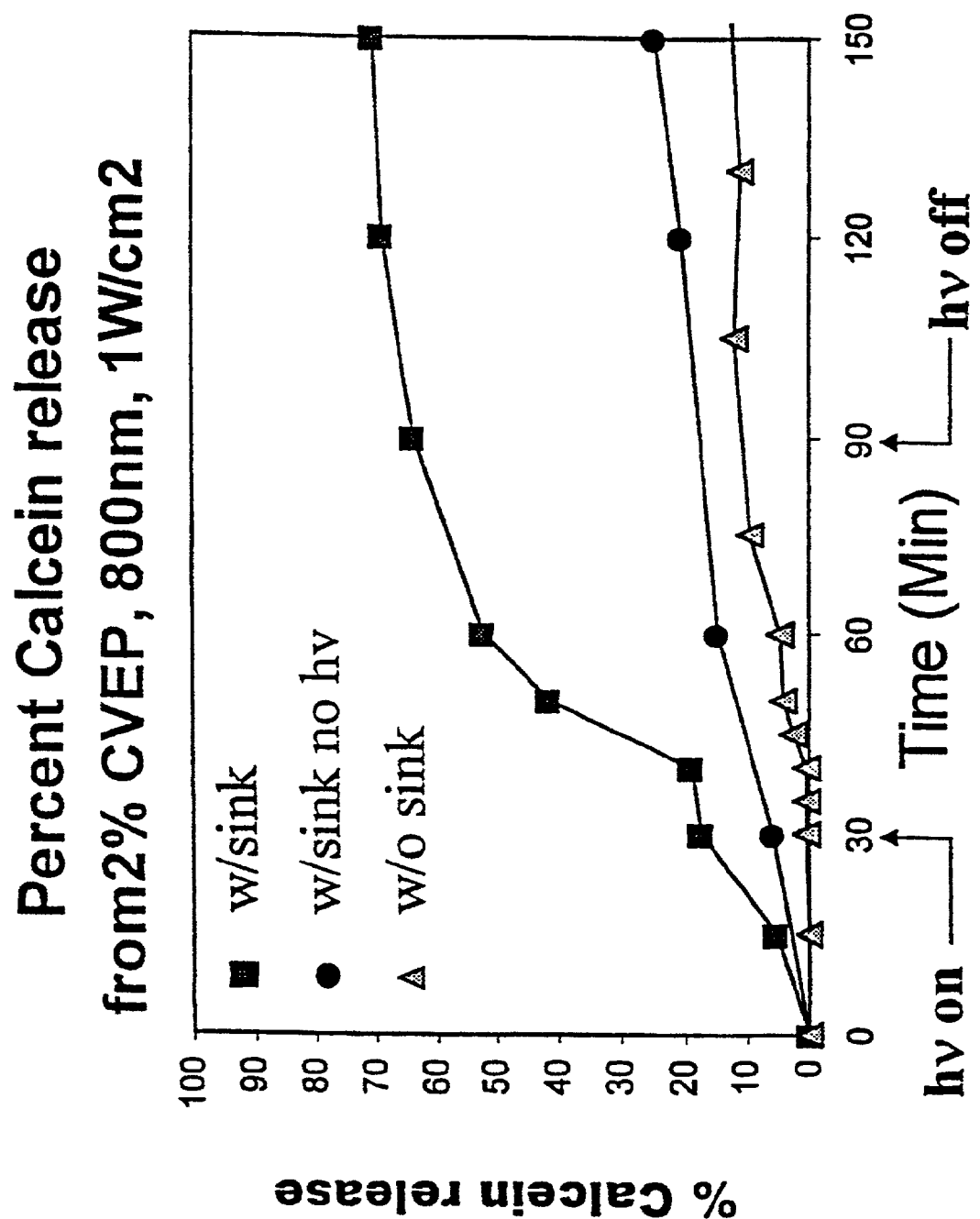
FIG. 6 is a comparison of photooxidatively triggered calcein release from CVEP:DOPE liposomes.
Figure 7:
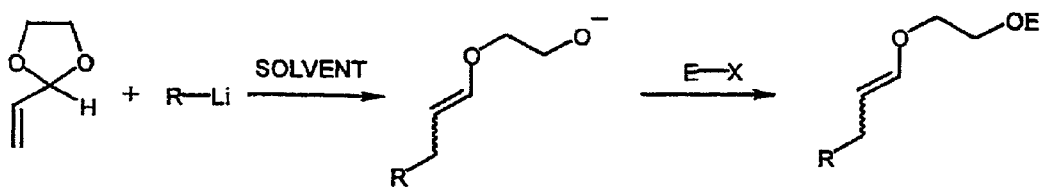
FIG. 7 is a flow chart of an alternative synthetic method for CVEP.

Oxidative Release. The release characteristics of 98:2 DOPE:CVEP:Bchla (pH 7.4) under photooxidative conditions is shown in FIG. 6. Irradiation of these vesicles lead to slow release in the absence of sink EPC, however, the observed release rate increased significantly when sink lipid was present. Background (dark) calcein leakage from the vesicles was not significant, even in the presence of sink EPC.

Cytoplasmic Delivery. DOPE:CVEP/calcein vesicles using folate as a targeting ligand (DSPE-PEG3350-folate)

initially revealed punctuated fluorescence, followed by diffuse cytoplasmic fluorescence. This was indicative of vesicle escape of calcein within the early endosome, which subsequently lead to endosomal escape at longer incubation times. Results from preliminary in vitro studies suggest that this may occur via vesicle-endosome membrane fusion.

Conclusions: The novel amphiphilic compounds shown in Series I–III, bearing hydrophilic headgroups that are linked to a hydrophobic membrane anchor via a water-soluble vinyl ether substituent, have been synthesized and their efficacy in acid- or oxidatively-activated release has demonstrated.

EXAMPLE 6

Comparative Cleavage Rates for CVEP and BVEP

BVEP, having two vinyl ether linkages, each bonding a hydrophobic tailgroup to a glycerol moiety, which in turn is bonded through an ester linkage to a polyethylene glycol hydrophilic headgroup is synthesized by known methods. See J. A. Boomer & D. H. Thompson, Chem. Phys. Lipids (1999) vol. 99, pg. 145–153.

Rates of cleavage by acid hydrolysis and oxidation are measured in a comparative study for CVEP and BVEP as follows:

Acid hydrolysis of CVEP and BVEP. Micellar solutions of the vinyl ether lipids are hydrolyzed at 37° C., pH 4.5 in 20 mM citrate buffered saline (150 mM). Samples of the hydrolysis mixture are periodically withdrawn and analyzed by HPLC ($C_{18}$ column, MeOH—$H_2O$ gradient, 1.5 ml/min). The disappearance of CVEP (retention time=34.7 min) due to acid-catalyzed hydrolysis is faster than the disappearance of BVEP (retention time=39–40 min) under the same experimental conditions.

Photooxidation of CVEP and BVEP. Micellar solutions of the vinyl ether lipids are photooxidized at 37° C. in the presence of bacteriochlorophyll a and air-saturated buffer (20 mM HEPES,150 mM NaCl, pH 7.4). Samples of the photolysis mixture are periodically withdrawn and analyzed by HPLC ($C_{18}$ column, MeOH—$H_2O$ gradient, 1.5 ml/min). The disappearance of CVEP (retention time=34.7 min) due to photolysis is faster than the disappearance of BVEP (retention time=39–40 min) under the same experimental conditions.

While the invention has been described in detail in the foregoing description, the same is to be considered as illustrative and not restrictive in character, it being understood that only the preferred embodiments have been described and that all changes and modifications that come within the spirit of the invention are desired to be protected.

We claim:

1. A vinyl ether lipid compound of the formula:

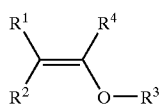

wherein one of either $R^1$ or $R^2$ is a hydrophilic headgroup and the other of $R^1$ or $R^2$ is hydrogen, a second hydrophilic headgroup, or a crosslinker joining at least one other molecule of the vinyl ether compound at the $R^1$ or $R^2$ position; $R^4$ is hydrogen or an electron donating group; and $R^3$ is cholesterol, a cholesterol derivative, sphingosine, a sphingosine derivative or a group according to the formula:

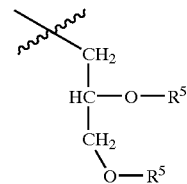

wherein each $R^5$ is independently a hydrophobic group of the formula:

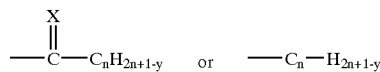

wherein X is O or S; n is an integer from 5 to 32 inclusive; y is an even integer from 2 to 12 inclusive; and y is less than or equal to n.

2. The compound according to claim 1 wherein $R^4$ is selected from the group consisting of $C_1$–$C_6$ alkoxy, furan, thiophene, methoxyphenyl, dimethoxyphenyl and trimethoxyphenyl.

3. The compound according to claim 1 wherein the hydrophilic headgroup is selected from the group consisting of poly(ethylene glycol), $C_1$–$C_6$ alkoxy poly(ethylene glycol), poly(ethylenimine), N,N-di(aminoethyl)carbamoyloxyethyl-, choline, monosaccharide, disaccharide, ethanolamine, phosphatidylcholine, phosphatidylethanolamine, cardiolipin, and phosphatidylmonosaccharides and phosphatidyldisaccharides.

4. The compound of claim 3, wherein the hydrophilic headgroup is poly(ethylene glycol), $C_1$–$C_6$ alkoxy poly (ethylene glycol) or poly(ethylenimine), N,N-di(aminoethyl)carbamoyloxyethyl-.

5. The compound of claim 3, wherein the hydrophilic headgroup is poly(ethylene glycol) or $C_1$–$C_6$ alkoxy poly (ethylene glycol) and the poly(ethylene glycol) moiety has an average of 1 to about 300 ethylene glycol units.

6. The compound according to claim 5 wherein the poly(ethylene glycol) moiety has an average of between about 10 and 150 ethylene glycol units.

7. The compound according to claim 1 wherein either $R^1$ or $R^2$ is poly(ethylene glycol), $C_1$–$C_6$ alkoxy poly(ethylene glycol) or poly(ethylenimine) or N,N-di(aminoethyl)carbamoyloxyethyl- and the other of $R^1$ or $R^2$ is hydrogen; and $R^3$ is selected from the group consisting of cholesterol, a cholesterol derivative and a group of the formula:

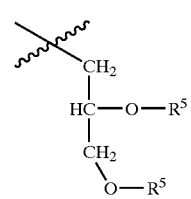

wherein each $R^5$ is independently a hydrophobic group of the formula:

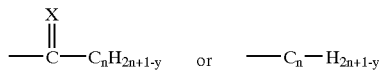

wherein X is O; n is an integer from 5 to 32 inclusive; y is an even integer from 2 to 12 inclusive; and y is less than or equal to n.

8. A vinyl ether lipid compound of the formula:

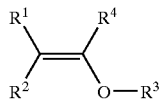

wherein one of either $R^1$ or $R^2$ is a hydrophilic headgroup and the other of $R^1$ or $R^2$ is hydrogen, a second hydrophilic headgroup, or a crosslinker joining at least one other molecule of the vinyl ether compound at the $R^1$ or $R^2$ position;

$R^3$ is an organic hydrophobic moiety; and $R^4$ is selected from the group consisting of $C_1$–$C_6$ alkoxy, furan, thiophene, methoxyphenyl, dimethoxyphenyl and trimethoxyphenyl.

9. The compound according to claim 8 wherein the hydrophilic headgroup is selected from the group consisting of poly(ethylene glycol), $C_1$–$C_6$ alkoxy poly(ethylene glycol), poly(ethylenimine), N,N-di(aminoethyl)carbamoyloxyethyl-, choline, monosaccharide, disaccharide, ethanolamine, phosphatidylcholine, phosphatidylethanolamine, cardiolipin, and phosphatidylmonosaccharides and phosphatidyldisaccharides.

10. The compound of claim 9, wherein the hydrophilic headgroup is poly(ethylene glycol), $C_1$–$C_6$ alkoxy poly(ethylene glycol) or poly(ethylenimine), N,N-di(aminoethyl)carbamoyloxyethyl-.

11. The compound of claim 10, wherein the hydrophilic headgroup is poly(ethylene glycol) or $C_1$–$C_6$ alkoxy poly(ethylene glycol) and the poly(ethylene glycol) moiety has an average of 1 to about 300 ethylene glycol units.

12. The compound according to claim 11 wherein the poly(ethylene glycol) moiety has an average of between about 10 and 150 ethylene glycol units.

13. The compound according to claim 8 wherein either $R^1$ or $R^2$ is poly(ethylene glycol), $C_1$–$C_6$ alkoxy poly(ethylene glycol) or poly(ethylenimine) or N,N-di(aminoethyl)carbamoyloxyethyl- and the other of $R^1$ or $R^2$ is hydrogen; and $R^3$ is selected from the group consisting of cholesterol, a cholesterol derivative and a group of the formula:

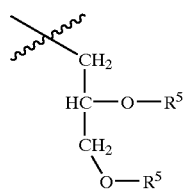

wherein each $R^5$ is independently a hydrophobic group of the formula:

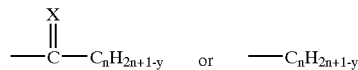

wherein X is O; n is an integer from 5 to 32 inclusive; y is an even integer from 2 to 12 inclusive; and y is less than or equal to n.

14. A vinyl ether lipid compound of the formula:

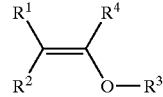

wherein each of $R^1$ or $R^2$ is independently a hydrophilic headgroup selected from the group consisting of poly(ethylene glycol), $C_1$–$C_6$ alkoxy poly(ethylene glycol), poly(ethylenimine), N,N-di(aminoethyl)carbamoyloxyethyl-, choline, monosaccharide, disaccharide, ethanolamine, phosphatidylcholine, phosphatidylethanolamine, cardiolipin, and phosphatidylmonosaccharides and phosphatidyldisaccharides;

$R^3$ is an organic hydrophobic moiety; and $R^4$ is an electron donating group.

15. The compound according to claim 14 wherein $R^3$ is selected from the group consisting of cholesterol, a cholesterol derivative and a group of the formula:

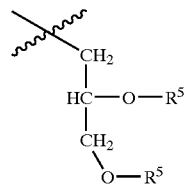

wherein each $R^5$ is independently a hydrophobic group of the formula:

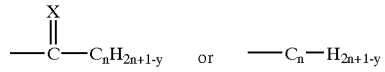

wherein X is O or S; n is an integer from 5 to 32 inclusive; y is an even integer from 2 to 12 inclusive; and y is less than or equal to n.

16. The compound according to claim 14 wherein $R^4$ is selected from the group consisting of $C_1$–$C_6$ alkoxy, furan, thiophene, methoxyphenyl, dimethoxyphenyl and trimethoxyphenyl.

17. The compound according to claim 15 wherein $R^4$ is selected from the group consisting of $C_1$–$C_6$ alkoxy, furan, thiophene, methoxyphenyl, dimethoxyphenyl and trimethoxyphenyl.

18. The compound according to claim 14 wherein said hydrophilic headgroups are selected from the group consisting of poly(ethylene glycol), $C_1$–$C_6$ alkoxy poly(ethylene glycol) or poly(ethylenimine), N,N-di(aminoethyl)carbamoyloxyethyl-.

19. A lipid vesicle comprising at least two different species of lipid compounds, at least one of said lipid compounds being a vinyl ether lipid compound according to claim 1.

20. A lipid vesicle comprising at least two different species of lipid compounds, at least one of said lipid compounds being a vinyl ether lipid compound according to claim 7.

21. A lipid vesicle comprising at least two different species of lipid compounds, at least one of said lipid compounds being a vinyl ether lipid compound according to claim 8.

22. A lipid vesicle comprising at least two different species of lipid compounds, at least one of said lipid compounds being a vinyl ether lipid compound according to claim 14.

23. The lipid vesicle according to any of claims 19–22 wherein said vinyl ether lipid compound comprises between about 0.1% and about 20% of the total molar lipid concentration of said vesicle.

24. The lipid vesicle of any of claims 19–23 wherein said vinyl ether lipid compound comprises between about 1% and about 15% of the total molar lipid concentration of said vesicle.

25. A method of delivering a therapeutic or diagnostic agent to a predetermined in vivo tissue or to the interior of a living cell, comprising contacting said tissue or cell with a liposome encapsulating said agent, under acidic or oxidative conditions, said liposome comprising at least two different species of lipid compounds, at least one of said lipid compounds being a vinyl ether lipid compound according to any of claim 1, 7, 8 or 14, said acidic or oxidative conditions being effective for cleaving said hydrophilic headgroup from said vinyl ether lipid compound.

26. A pharmaceutical composition comprising a therapeutic or diagnostic agent encapsulated in a lipid vesicle according to any of claims 19–22 in a pharmaceutically acceptable carrier.

* * * * *